United States Patent [19]

Gardner et al.

[11] Patent Number: 4,868,176

[45] Date of Patent: Sep. 19, 1989

[54] NOVEL IMIDAZOBENZODIAZEPINES

[75] Inventors: Colin R. Gardner, Newbury; Charles John R. Hedgecock, Bassett, both of Great Britian

[73] Assignee: Roussel Uclaf, Paris, France

[21] Appl. No.: 237,508

[22] Filed: Aug. 26, 1988

[30] Foreign Application Priority Data

Aug. 28, 1987 [GB] United Kingdom ................. 8720414

[51] Int. Cl.⁴ ..................... A61K 31/55; C07D 487/04
[52] U.S. Cl. ................................... 514/220; 514/219; 540/494; 540/498
[58] Field of Search ................ 540/494, 498; 514/220, 514/219

[56] References Cited

U.S. PATENT DOCUMENTS 4,359,420 11/1982 Gerecke et al. .................... 540/498

Primary Examiner—Robert T. Bond
Attorney, Agent, or Firm—Bierman and Muserlain

[57] ABSTRACT

A compound selected from the group consisting a compound of the formula

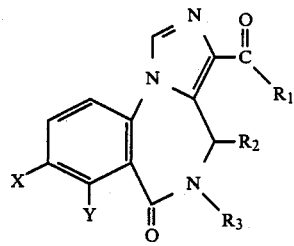

wherein $R_1$ is selected from the group consisting of phenyl, cycloalkyl of 4 to 6 carbon atoms and

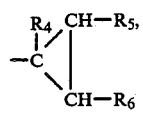

$R_4$ and $R_5$ are individually hydrogen or alkyl of 1 to 5 carbon atoms, $R_6$ is selected from the group consisting of hydrogen, alkyl of 1 to 5 carbon atoms, phenyl, halogen, alkoxycarbonyl of 2 to 5 carbon atoms, cyano, amido and mono- and dialkylamido of 1 to 5 alkyl carbon atoms, $R_2$ and $R_3$ are individually selected from the group consisting of hydrogen, alkyl of 1 to 5 carbon atoms and cycloalkyl of 3 to 5 carbon atoms or taken together form alkylene of 3 to 5 carbon atoms, X and Y are individually selected form the group consisting of hydrogen, halogen, $-NO_2$, azido, $-CN$, $-CF_3$ and alkyl and alkoxy of 1 to 3 carbon atoms and their nontoxic, pharmaceutically acceptable acid addition salts capable of inducing an affinity for benzodiazepine receptors and a novel process and novel intermediates for their preparation.

13 Claims, No Drawings

NOVEL IMIDAZOBENZODIAZEPINES

OBJECTS OF THE INVENTION

It is an object of the invention to provide the novel imidazobenzodiapines of formula I and their non-toxic, pharmaceutically acceptable acid addition salts and a process and intermediates for their preparation.

It is another objects of the invention to provide compositions for inducing an affinity for benzodiazepine receptors and a method of inducing such activity in warm-blooded animals.

These and other objects and advantages of the invention will become obvious from the following detailed description.

THE INVENTION

The novel compounds of the invention are compounds selected from the group consisting of a compound of the formula

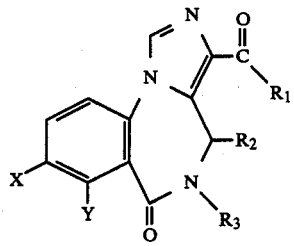

I wherein $R_1$ is selected from the group consisting of phenyl, cycloalkyl of 4 to 6 carbon atoms and

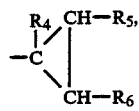

$R_4$ and $R_5$ are individually hydrogen or alkyl of 1 to 5 carbon atoms, $R_6$ is selected from the group consisting of hydrogen, alkyl of 1 to 5 carbon atoms, phenyl, halogen, alkoxycarbonyl of 2 to 5 carbon atoms, cyano, amido and mono- and dialkylamido of 1 to 5 alkyl carbon atoms, $R_2$ and $R_3$ are individually selected from the group consisting of hydrogen, alkyl of 1 to 5 carbon atoms and cycloalkyl of 3 to 5 carbon atoms or taken together from alkylene of 3 to 5 carbon atoms, X and Y are individually selected from the group consisting of hydrogen, halogen, —$NO_2$, azido, —CN, —$CF_3$ and alkyl and alkoxy of 1 to 3 carbon atoms and their non-toxic, pharmaceutically acceptable acid addition salts.

Examples of alkyl of 1 to 5 carbon atoms are methyl, ethyl, n-propyl, isopropyl, butyl, tert.-butyl, isobutyl and pentyl. Examples of halogens are flourine, bromine, and chlorine. Methoxycarbonyl, ethoxycarbonyl and propoxycarbonyl are examples of alkoxycarbonyl of 2 to 5 carbon atoms and examples of mono- and dialkylamido group of 1 to 5 alkyl carbon atoms are monomethylamido, dimethylamido, monoethylamido, diethylamido, monopropylamido and dipropylamido.

Examples of suitable acids for the formation of non-toxic, pharmaceutically acceptable acid addition salts are inorganic acids such as hydrochloric acid, hydrobromic acid, hydroiodic acid, nitric acid, sulfuric acid and phosphoric acids and organic acids such as acetic acid, propionic acid, formic acid, benzoic acid, maleic acid, fumaric acid, succinic acid, tartaric acid, citric acid, oxalic acid, glyoxylic acid or aspartic acid, or alkanesulfonic acids such as methanesulfonic acid or arylsulfonic acids such as benzene sulfonic acid.

Among the preferred compounds of formula I are those wherein $R_1$ is cyclopropyl, those wherein $R_2$ and $R_3$ are individually hydrogen or methyl and those wherein X and Y are individually hydrogen, fluorine or bromine and their non-toxic, pharmaceutically acceptable acid addition salts. Especially preferred is 3-(5,6-dihydro-5-methyl-6-oxo-4H-imidazo[1,5a] [1,4]-benzodiazepinyl)-cyclopropylmethanone and its salts.

The novel process of the invention for the preparation of a compound of the formula

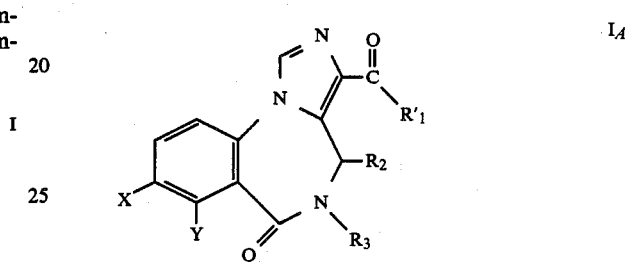

$I_A$ wherein $R_2$, $R_3$, X and Y are as defined above and $R_1'$ is selected from the group consisting of cycloaklyl of 4 to 6 carbon atoms phenyl and

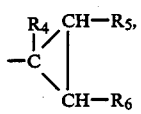

$R_4$ is hydrogen and $R_5$ and $R_6$ are individually hydrogen or alkyl of 1 to 5 carbon atoms comprising reacting a compound of the formula

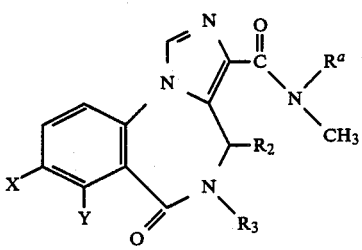

III wherein $R_2$, $R_3$, X and Y are as defined above and $R^a$ is methyl or methoxy with a compound of the formula

IV wherein M is an alkali metal such as lithium or —Mg—Hal, Hal is chlorine, bromine or iodine. The reaction is preferably effected in an organic solvent such as anhydrous tetrahydrofuran.

The compounds of formula III may be prepared by reacting a compound of the formula

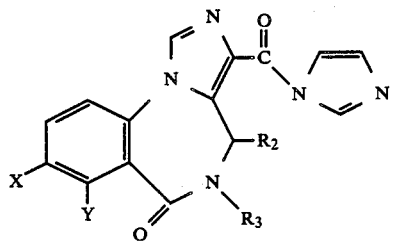

wherein X, Y, R₂ and R₃ are as defined above with a compound of the formula

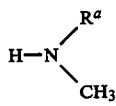

wherein $R^a$ is methyl or methoxy or an acid addition salt thereof. Reaction is preferably effected with dimethylformamide as solvent. The compounds of formula V maybe prepared by the process of European Pat. No. 109,921.

The compounds of formula $I_A$ may also be prepared by oxidation of a compound of the formula

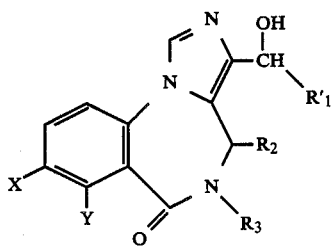

wherein $R_1$, $R_2$, $R_3$, X and Y are as defined above. The oxidation is preferably effected with manganese dioxide, nitric acid, ferric chloride or chromium oxide in the presence of pryridine, by Oppenauer oxidation or by dehydrogenation in the presence of a copper catalyst.

The compounds of formula VII may, for example, be prepared by reacting a compound of the formula

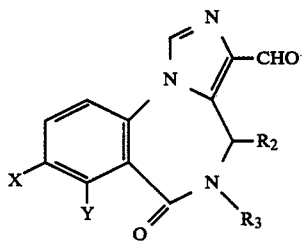

wherein X, Y, R₂ and R₃ are as defined above with a compound of the formula

wherein M and $R_1'$ are as defined above. The said reaction is preferably effected under anhydrous conditions and in an organic solvent such as tetrahydrofuran. The compounds of formula VIII may, for example, be prepared as shown in published European Patent Application No. 0,027,214.

The process for the preparation of compounds of the formula

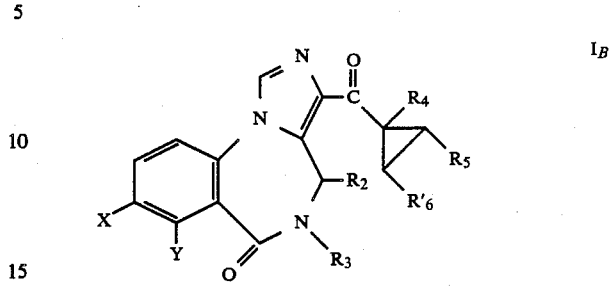

wherein $R_2$, $R_3$, $R_4$, $R_5$, X and Y are as defined above and $R_6'$ is hydrogen, halogen, alkyl of 1 to 5 carbon atoms, an alkoxycarbonyl group of 2 to 5 carbon atoms or phenyl comprises reacting a compound of the formula

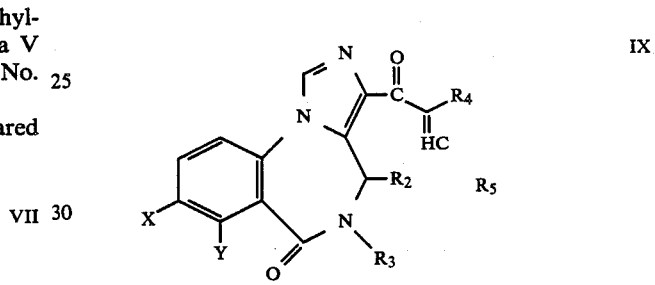

wherein $R_2$, $R_3$, $R_4$, $R_5$, X and Y are as defined above with an appropriate cyclizing reagent. The cyclizing reagent will be a reagent serving to introduce a group

across the vinylic double bond.

When a compound of formula $I_B$ wherein $R_4$ is alkyl of 1 to 5 carbon atoms and $R_5$ is hydrogen and $R_6'$ is hydrogen or alkyl of 1 to 5 carbon atoms is desired, the cyclization is advantageously effected with trialkylsulfoxonium iodide in the presence of an organic solvent such as dimethylformamide. When a compound of formula $I_B$ wherein $R_4$ is hydrogen, $R_5$ is alkyl of 1 to 5 carbon atoms and $R_6'$ is hydrogen or alkyl of 1 to 5 carbon atoms is desired, the cyclization is advantageously effected with dimethylaminoalkylphenyloxosulfonium tetrafluoroborate in the presence of an organic solvent such as dimethylformamide.

When a compound of formula $I_B$ wherein $R_4$ is hydrogen and $R_6'$ is alkoxycarbonyl or phenyl is desired, the cyclization is advantageously effected by means of a dimethylsulfuranylidiene acetate or benzyl dimethyl sulfonium anion in the presence of an organic solvent such as chloroform. When a compound of formula $I_B$ wherein $R_4$ is hydrogen and $R_6'$ is halogen is desired, the cyclization is advantageously effected by means of a dimethylaminophenyloxo sulfonium halomethylylide in the presence of an organic solvent such as dimethylformamide.

The compounds of formula IX may, for example, be prepared by reaction of a compound of formula III with a compound of the formula

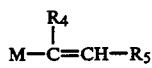   X wherein M, R$_4$ and R$_5$ are as defined above. The said reaction is preferably effected under anhydrous conditions and in an organic solvent such as tetrahydrofuran.

Alternatively, the compounds of formula IX may, for example, be prepared by oxidation of a compound of the formula

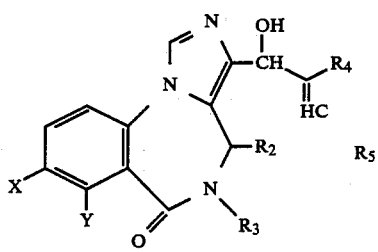   XI wherein R$_2$, R$_3$, R$_4$, R$_5$, X and Y are as defined above. The said oxidation of the compound of formula XI is preferably effected with manganese dioxide, nitric acid, ferric chloride or chromium oxide, in the presence of pyridine, or by Oppenauer oxidation or by dehydrogenation in the presence of a copper catalyst.

The compounds of formula XI may, for example, be prepared by reacting a compound of the formula

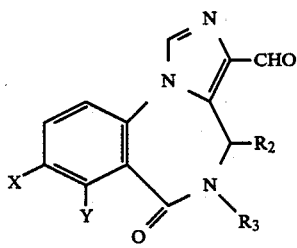   VIII wherein R$_2$, R$_3$, X and Y are defined above with a compound of the formula

   X wherein M, R$_4$ and R$_5$ are as defined above. The said reaction is preferably effected under anhydrous conditions and in an organic solvent such as tetrahydrofuran.

The process for the preparation of compounds of the formula

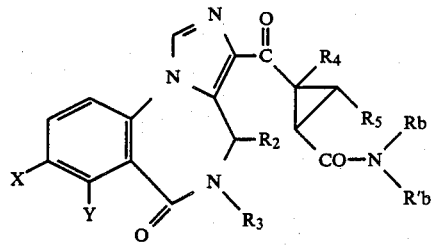   I$_C$ wherein R$_2$, R$_3$, R$_4$, R$_5$, X and Y are as defined above and Rb and R'b are individually hydrogen or alkyl of 1 to 5 carbon atoms may, for example, be prepared by reacting a compound of the formula

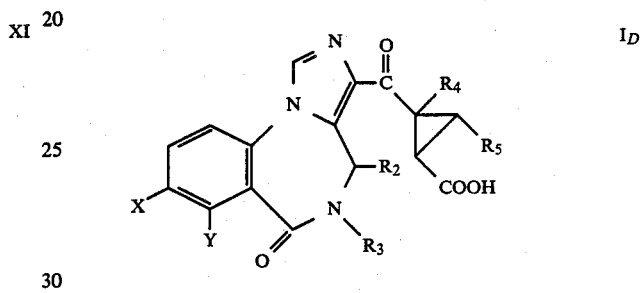   I$_D$ wherein R$_2$, R$_3$, R$_4$, R$_5$, X and Y are as defined above with a compound of the formula

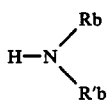   XII wherein Rb and R'b are as defined above. The said reaction is preferably effected in an anhydrous organic solvent in the presence of carbonyldiimidazole.

The compounds of formula I$_D$ may, for example, be prepared by saponification of a compound of the formula

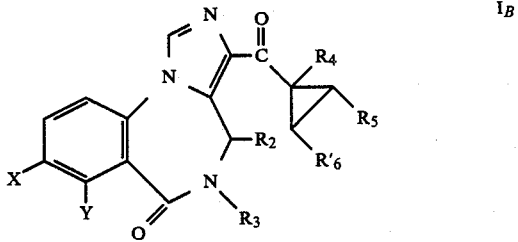   I$_B$ wherein R$_2$, R$_3$, R$_4$, R$_5$, X and Y are as defined above and R$_6'$ is alkoxycarbonyl of 2 to 5 carbon atoms. The saponification is preferably effected in an alkali metal hydroxide such as sodium hydroxide.

The process for the preparation of compounds of the formula

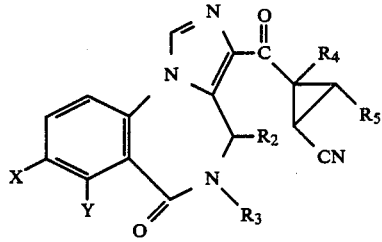

wherein R₂, R₃, R₄, R₅, X and Y are as defined above may, for example, be prepared by dehydration of a compound of the formula

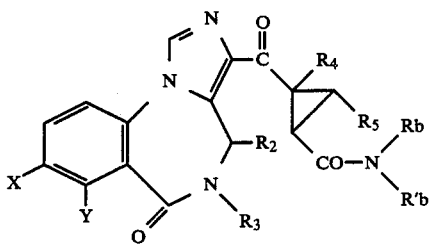

wherein R₂, R₃, R₄, R₅, X and Y are as defined above and Rb and R'b each is hydrogen. The dehydration is preferably effected with the anhydride of a strong acid such as trifluoroacetic acid anhydride in the presence of an organic solvent such as dichloromethane.

The compounds of formula I are basic in character and may thus, if desired, be converted into their acid addition salts. The acid addition salts of the compounds of formula I are advantageously prepared by reacting, in approximately stoichiometric proportions, an inorganic or organic acid with the compound of formula I. The salts may be prepared without intermediate isolation of the corresponding base.

The novel compositions of the invention for inducing an affinity for benzodiazepine receptors comprise an effective amount of at least one compound of formula I and their non-toxic, pharmaceutically acceptable acid addition salts sufficient to induce such activity and an inert pharmaceutical carrier or excipient. The compositions may be in the form of tablets, dragees, capsules, granules, suppositories and injectable solutions or suspensions.

Examples of suitable excipients are talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents, preservatives.

The compositions of the invention possess very interesting pharmacological properties; particularly weak inverse agonist properties of the compounds and longer duration of action of all the compounds compared to similar reported imidazobenzodiazepines. In addition, some of the compounds possess tranquillizing properties. They are useful, for example, in the treatment of memory disorders, particularly in geriatrics, and in cerebral sensecence disorders. Certain compounds may also be used in the treatment of obesity and as minor tranquillizers in the treatment of certain agitated or irritated conditions, and certain forms of epilepsy.

The novel method of the invention of inducing an affinity for benzodiazepine receptors in warm-blooded animals, including humans, comprises administering to warm-blooded animals an amount of at least one compound of formula I and their non-toxic, pharmaceutically acceptable acid addition salts sufficient to induce said activity. The compounds may be administered orally, rectally or parenterally and the usual daily does is 0.001 to 2.85 mg/kg depending on the specific compound, the method of administration and the condition treated.

The novel intermediates of the invention are those of formulae VII, XI, IX, III and I$_D$.

In the following examples there are described several preferred embodiments to illustrate the invention. However, it should be understood that the invention is not intended to be limited to the specific embodiments.

EXAMPLE 1

3-(5,6-dihydro-5-methyl-6-oxo-4H-imidazol[1,5a][1,4-]benzodiazepinyl)-cyclopropylmethanone

STEP A:

3-(5,6-dihydro-5-methyl-6-oxo4H-imidazol[1,5a][1,4-]benzodiazepinyl)-cyclopropylmethanol To 1.82 g (7.55 mmol) of 5,6-dihydro-5-methyl-6-oxo-4H-imidazo[1,5a][1,4]benzodiazepine-3-carboxaldehyde in 50 ml of dry THF, 22.7 ml of a 0.5M solution of cyclopropyl magnesium bromide in THF were added dropwise with stirring at ambient temperature. After reflux for 30 minutes, a further portion of 11.4 ml. of cyclopropyl grignard were added and the reaction mixture was stirred at ambient temperature for 18 hours. The resultant suspension was poured into 100 ml of ice/water, filtered through Celite and the THF removed under vacuum. Extraction with chloroform (3×70 ml), washing the extracts with brine and drying over MgSO₄ gave 2.5 g. of a yellow oil. Flash chromatography (SiO₂, CHCl₃+4% MeOH) yielded 1.47 g. of pure expected product (69% yield) melting at 126 to 128° C. (ethyl acetate/60 to 80° C. pet. ether).

NMR (CDCl₃): 8.05(d.d); 7.86(s); 7.61(d.t); 7.49(d.t); 7.40(d.d); 4.30–4.68 br. 2H); 4.19(d.d); 3.24(S,MeN); 1.39(m); 0.68 and 0.50 (2×m, 2×2H).

IR Spectrum (KBr): 3360 br; 1640; 1630; 1495; 1395; 1225; 1033; 942; 760 cm⁻¹.

STEP B:

3-(5,6-dihydro-5-methyl-6-oxo-4H-imidazo[1,5a][1,4-]benzodiazepinyl)-cyclopropylmethanone 1.87 g (6.61 mmol) of 3-(5,6-dihydro-5-methyl-6-oxo-4H-imidazo[1,5a][1,4]benzodiazepinyl)-cyclopropylmethanol in 120 ml of methylene chloride were stirred with 5.75 g of manganese IV oxide. After one hour, a further 5.75 g of MnO₂ were added and after a further 2 hours, the solution was filtered through Celite and washed with 10% methanol in CH₂Cl₂. The crude product was concentrated in vacuum and purified by flash chromatography (SiO₂, CHCl₃). Crystallization from hot ethyl acetate gave 1.27 g of the expected products as shiny white platelets (68% yield) melting at 191°–193° C.

MNR (CDCl₃): 8.05(d.d); 7.88(s); 7.63(d.t); 7.53(d.t); 7.41(d.d); 5.28 and 4.33 (2+ br. 2H); 3.23 (s, 3H); 3.18(m); 1.25(br, 2H); and 1.08(br, 2H).

IR Spectrum (KBr): 3100; 1735; 1565; 1495; 1390; 1250; 1230; 755 cm⁻¹.

Analysis: $C_{16}H_{15}N_3O_2$: Calculated: % C; 68.31, % H; 5.37, % N; 14.94, Found: % C; 68.38, % H; 5.43, % N; 14.94.

EXAMPLE 2

(8-Chloro-5,6-dihydro-5-methyl-6-oxo-4H-imidazo[1,5-a][1,4]benzodiazepin-3-yl)-cyclopropylmethanone

STEP A: Methyl (8-chloro-5,6-dihydro-5-methyl-6-oxo-4H-imidazo[1,5-a][1,4]benzodiazepin-3-yl)-N-methyl-carbohydroxamate (Preparative Example A)

To 4.26 g. (1.46 mmol) of 8-chloro-5,6-dihydro-5-methyl-6-oxo-4H-imidazo[1,5-a][1,4]-benzodiazine-3-carboxylic acid dissolved in 70 ml of DMF, there was added 3 equiv. or 7.12 g of 1,1'-carbonyldiimidazole. After stirring at 50° C. for 3 hours, the reaction was cooled in an ice-bath and the white solid was filtered off to obtain 3.79 g of imidazolide (76% yield) which was used directly in the next step.

Thus of the 3.79 g (11.1 mmol) of the imidazolide in 75 ml of DMF was warmed with stirring to 60° C. with 3.25 g, (33.3 mmol) of N,0-dimethylhydroxylamine hydrochloride. After 1½ hours, the reaction was poured into 300 ml of water and was extracted with ethyl acetate (33×100 ml). Drying over MgSO₄, filtering and concentration in vacuo gave a first crop of 2.89 g of crystallization expected product. Further concentration gave a second crop of 255 mg (85% yield).

STEP B: (8-chloro-5,6-dihydro-5-methyl-6-oxo-4H-imidazo[1,5-a][1,4]benzodiazepin-3-yl)-cyclopropylmethanone To a solution of 14.1 mmol of cyclopropylmagnesium bromide in 20 ml of dry THF, there was added a solution of methyl (8-chloro-5,6-dihydro-5-methyl-6-oxo-4H-imidazo[1,5-a][1,4]benzodiazepin-3-yl) N-methyl carbohydroxamate in 20 ml of dry TFH with cooling in a water bath. After stirring at ambient temperature for 80 minutes, the reaction was quenched with ammonium chloride solution and extracted with chloroform. The extracts were dried over MgSO₄, evaporated to an oil and purified by flash chromatography in methylene chloride/ethyl acetate Crystallization from ethyl acetate gave 704 mg. (48% yield) of the expected product as white crystals melting at 230°–232° C.

The following N-methyl-carbohydroxamate derivatives were prepared using the procedure of Step A of Example 1:

Preparative Example B (5,6-Dihydro-5-methyl-6-oxo-4H-imidazo[1,5-a][1,4]-benzodiazepin-3-yl)-N-methyl carbohydroxamate.

Preparative Example C (5,6-Dihydro-8-fluoro-5-methyl-6-oxo-4H-imidazo[1,5-a][1,4]-benzodiazepin-3-yl)-N-methyl carbohydroxamate.

Preparative Example D (8-Bromo-5,6-dihydro-5-methyl-6-oxo-4H-imidazo[1,5-a][1,4]-benzodiazepin-3-yl)-N-methyl carbohydroxamate.

The following cyclopropylmethanone derivatives were prepared using the procedure of Example 2:

EXAMPLE 3

(5,6-Dihydro-8-fluoro-5-methyl-6-oxo-4H-imidazo[1,5-a][1,4]benzodiazepin-3-yl)-cyclopropylmethanone

EXAMPLE 4

(8-Bromo-5,6-dihydro-5-methyl-6-oxo-4H-imidazo[1,5-a][1,4]benzodiazepin-3-yl)-cyclopropylmethanone The following phenylmethanone derivatives were prepared in a similar manner to Example 2, using phenyl magnesium bromide in place of cyclopropylmagnesium bromide.

EXAMPLE 5

(5,6-Dihydo-5-methyl-6-oxo-4H-imidazo[1,5-a][1,4]benzodiazepin-3-yl)phenylmethanone

EXAMPLE 6

(5,6-Dihydro-8-fluoro-5-methyl-6-oxo-4H-imidazo[1,5-a][1,4]benzodiazepin-3-yl)phenylmethanone

EXAMPLE 7

(8Chloro-5,6-dihydro-5-methyl-6-oxo-4H-imidazo[1,5-a][1,4]benzodiazepin-3-yl)phenylmethanone

EXAMPLE 8

(8-Bromo-5,6-dihydro-5-methyl-6-oxo-4H-imidazo[1,5-a][1,4]benzodiazepin-3-yl)phenylmethanone

EXAMPLE 9

Tablets were prepared containing 20 mg. of the compound of Example 1 and sufficient excipient of lactose, starch, talc, magnesium stearate for a tablet weighing 150 mg.

[Structure: imidazole-N-CH2-C(=C(COR1))- attached to benzamide N(CH3) with X on benzene ring]

| Example | R₁—CO— | X | Yield | mp °C | IR cm⁻¹ | NMR | Formula m/e | C Calc Found | H | N | X |
|---|---|---|---|---|---|---|---|---|---|---|---|
| 1 | cyclopropyl-C(=O)- | H | 47%^A | 191-193 EtOaC | 3100,1641,1565,1495, 1390,1230,755 | 7.41-8.05 (aromatic, 3H); 5.28 & 4.33 (br, 2H); 3.23 (s, 3H); 3.18 (m, 1H) 1.25 (m, 2H); 1.08 (m, 2H) | C₁₆H₁₅N₃O₂ 281.32 | 68.31 68.38 | 5.37 5.43 | 14.94 14.94 | — |
| 3 | " | F | 58%^B | 185-187 | | 7.40-8.05 (aromatic, 4H); 5.33 & 4.35 (br, 2H); 3.23 (s, 3H); 3.18 (m, 1H); 1.23 (m, 2H); 1.09 (m, 2H) | C₁₆H₁₄FN₃O₂ 299.31 | 64.20 63.80 | 4.72 4.81 | 14.03 13.79 | 6.35 6.21 |
| 2 | " | Cl | 48%^B | 230-232 | | | C₁₆H₁₄ClN₃O₂ 315.75 | 60.86 | 4.48 | 13.30 | 11.23 |
| 4 | " | Br | 58%^B | 228-230 | 3100,1637,1490,1392, 1248,1218,938 | 7.28-8.20 (aromatic, 4H); 5.32 & 4.30 (br, 2H); 3.24 (s, 3H); 3.20 (m, 1H); 1.25 (m, 2H); 1.11 (m, 2H) | C₁₆H₁₄BrN₃O₂ 360.218 | 53.35 | 3.92 | 11.67 | 22.18 |
| B | Me-N(Me)-C(=O)- | H | | | | 7.43-8.08 (aromatic, 3H); 4.33 & 5.20 (br, 2H); 3.93 (s, 3H); 3.58 (s, 3H); 3.30 (s, 3H) | | | | | |
| C | " | F | 67%^C | 176-177 | | | C₁₅H₁₅FN₄O₃ 318.31 | 56.60 56.48 | 4.76 4.82 | 17.59 17.46 | 5.97 5.96 |
| A | " | Cl | 85%^C | 160-161 | | | C₁₅H₁₅ClN₄O₃ 334.75 | 53.82 53.61 | 4.53 4.57 | 16.73 16.69 | 10.59 |
| D | " | Br | 76%^C | 179-180 | 3110,1635,1580 1496,1386,1229,942 | 7.31-8.19 (aromatic, 4H); 5.20 & 4.30 (br, 2H); 3.92 (s, 3H); 3.57 (s, 3H); 3.28 (s, 3H) | C₁₅H₁₅BrN₄O₃ 379.221 | 47.51 47.51 | 3.99 4.00 | 14.77 14.67 | 21.07 21.30 |
| 5 | Ph-C(=O)- | H | | | | | | | | | |
| 6 | " | F | 69%^B | | | | C₁₉H₁₄FN₃O₂ 335.33 | 68.05 | 4.22 | 12.52 | 5.67 |
| 7 | " | Cl | 82%^B | | | | C₁₉H₁₄ClN₃O₂ 351.78 | 64.87 64.77 | 4.02 4.13 | 11.94 11.84 | 10.08 10.22 |
| 8 | " | Br | 41%^B | 220-223 | 3120,1630,1542, 1494,1363,1285,902 | 7.30-8.28 (aromatic, 9H); 5.35 & 4.43 (b, 2H); 3.30 (s,3H) | C₁₉H₁₄BrN₃O₂ 396.25 | 57.59 57.68 | 3.56 3.72 | 10.60 10.40 | 20.17 19.97 |

A - from aldehyde   B - from hydroxarate   C - from imidazole

Pharmacological Activity

The compounds are agents which interact with benzodiazepine receptors in the brain, some being useful for the treatment of obesity or cognitive impairment and some being useful as minor tranquillizers. Screening for benzodiazepione receptor binding (BRB) was carried out by the method described in British Pat. No. 2,128,989.

The ability of the compounds to induce twitch in the hyoidal muscle of rats was studied according to the method of W. James et al (Eur. J. Pharmacol (1985) Vol. 113, p. 233).

Potentiation of the threshold of leptazol induced seizures in mice by active compounds was measured by the method of Lichfiel et al (J. Pharmacol. Exp. Ther. (1949) Vol. 96 Page. 99). The results are as follows:

| Compound | BRBnM | Hyoidal Twitch mg/kg | Leptazol Seizures $ED_{50}$ mg/kg |
|---|---|---|---|
| 1 | 95 | 20 ip (+) | 1-2 ip |
| 2 | 64 | 50 ip ++ | Not active |
| 3 | 560 | | |
| 4 | 354 | | |
| 6 | >10,000 | | |
| 10 | 10,000 | | |
| 11 | 3,500 | | |
| 12 | 10,000 | | |

Various modifications of the products and processes of the invention may be made without departing from the spirit or scope thereof and it should be understood that the invention is intended to be limited only as defined in the appended claims.

What we claim is:

1. A compound selected from the group consisting of a compound of the formula

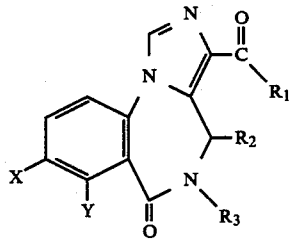

I wherein $R_1$ is selected from the group consisting of phenyl, cycloalkyl of 4 to 6 carbon atoms and

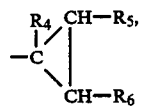

$R_4$ and $R_5$ are individually hydrogen or alkyl of 1 to 5 carbon atoms $R_6$ is selected from the group consisting of hydrogen, alkyl of 1 to 5 carbon atoms, phenyl, halogen, alkoxycarbonyl of 2 to 5 carbon atoms, cyano, amido and mono- and diialkylamido of 1 to 5 alkyl carbon atoms, $R_2$ and $R_3$ are individually selected from the group consisting of hydrogen, alkyl of 1 to 5 carbon atoms and cycloalkyl of 3 to 5 carbon atoms or taken together form alkylene of 3 to 5 carbon atoms, X and Y are individually selected from the group consisting of hydrogen, halogen, —$NO_2$, azido, —CN, —$CF_3$ and alkyl and alkoxy of 1 to 3 carbon atoms and their non-toxic, pharmaceutically acceptable acid addition salts.

2. A compound of claim 1 wherein $R_1$ is cyclopropyl.

3. A compound of claim 2 wherein $R_2$ and $R_3$ are individually hydrogen or methyl and X and Y are individually hydrogen, fluorine or bromine.

4. A compound of claim 1 selected from the group consisting of 3-(5,6-dihydro-5-methyl-6-oxo-4H-imidazo[1,5-a][1,4]benzodiazepinyl)-cyclopropylmethanone and its non-toxic, pharmaceutically acceptable acid addition salts.

5. A composition for inducing an affinity for benzodiazepine receptors comprising an amount of at least one compound of claim 1 for inducing an affinity for benzodiazepine receptors and an inert pharmaceutical carrier.

6. A composition of claim 5 wherein in the active compound $R_1$ is cyclopropyl.

7. A composition of claim 6 wherein in the active compound $R_2$ and $R_3$ are individually hydrogen or methyl and X and Y are individually hydrogen, fluorine or bromine.

8. A composition of claim 5 wherein the active compound is selected from the group consisting of 3-(5,6-dihydro-5methyl-6-oxo-4H-imidazo[1,5-a][1,4]benzodiazepinyl)-cyclopropylmethanone and its non-toxic, pharmaceutically acceptable acid addition salts.

9. A method of inducing an affinity for benzodiazepine receptors in warm-blooded animals comprising administering to warm-blooded animals an amount of at least one compound of claim 1 sufficient to induce an affinity for benzodiazepine receptors.

10. A method of claim 9 wherein in the active compound $R_1$ is cyclopropyl.

11. A method of claim 10 wherein in the active compound $R_2$ and $R_3$ are individually hydrogen or methyl and X and Y are individually hydrogen, fluorine or bromine.

12. A method of claim 9 wherein the active compound is selected from the group consisting of 3-(5,6-dihydro-5-methyl-6-oxo-4H-imidazo[1,5-a][1,4]benzodiazepinyl)-cyclopropylmethanone and its non-toxic, pharmaceutically acceptable acid addition salts.

13. A compound having a formula selected from the group consisting of

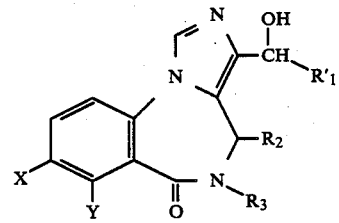

VII

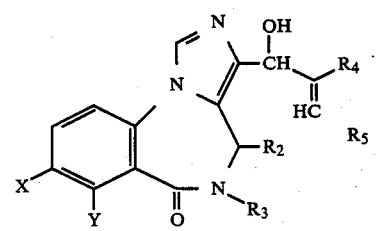

XI

-continued
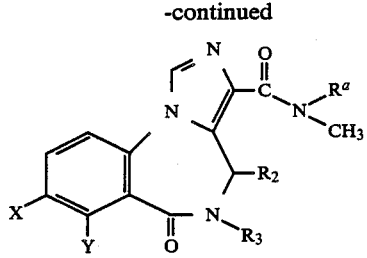
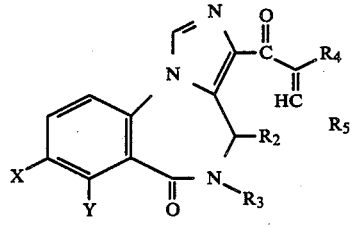
and
-continued
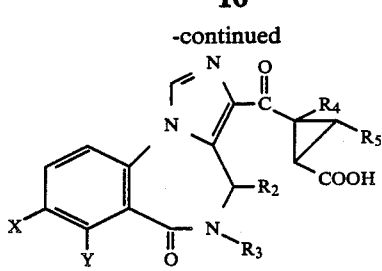
wherein X, Y, $R_2$, $R_3$, $R_4$ and $R_5$ have the definition of claim 1, $R_1'$ is selected from the group consisting of cycloalkyl of 4 to 6 carbon atoms, phenyl and
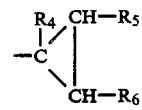
wherein $R_4$ is hydrogen and $R_5$ and $R_6$ are hydrogen or alkyl of 1 to 5 carbon atoms and $R^a$ is methyl or methoxy.
* * * * *

UNITED STATES PATENT AND TRADEMARK OFFICE
CERTIFICATE OF CORRECTION

PATENT NO. : 4,868,176

DATED : Sept 19, 1989

INVENTOR(S) : Colin R. Gardner, Charles John R. Hedgecock

It is certified that error appears in the above-identified patent and that said Letters Patent is hereby corrected as shown below:

Column 2, line 61, "-Mg-  should be -- Mg-Hal --
                    Hal"
In each of the formulas:
Col. 4, Formula IX
Col. 5, Formula XI
Col. 14, Formula XI, claim 13
Col. 15, Formula IX, claim 13 between "HC" and "R$_5$" insert the following -- $\ell$ --.

UNITED STATES PATENT AND TRADEMARK OFFICE
CERTIFICATE OF CORRECTION

PATENT NO. : 4,868,176

DATED : Sept. 19, 1989

INVENTOR(S) : Colin R. Gardner, Charles John R. Hedgecock

It is certified that error appears in the above-identified patent and that said Letters Patent is hereby corrected as shown below:

| Col. | Line | |
|---|---|---|
| 8 | 19 | "[1,4 ]" ahould be --[1,4]-- |
| 8 | 23 | " " " " " " " " " " " " " " |
| 8 | 43 | " br. 2H)" should be --(br. 2H)-- |
| 8 | 49 | "[1,4 ]" should be --[1,4]-- |
| 9 | 6 | "[1,5-a]" should be --[1,5-a]-- |
| 9 | 10 | " " " " " " " " " " " " " " |
| 9 | 33 | " " " " " " " " " " " " " " |
| 10 | 19&20 | "[1,5-a]" should be [1,5-a]-- |
| 10 | 22&23 | " " " " " " " " " " " " " |
| 10 | 35&36 | " " " " " " " " " " " " " |
| 10 | 39&40 | " " " " " " " " " " " " " |
| 10 | 42&43 | " " " " " " " " " " " " " |
| 14 | Claim 13 | Same Formula as XI Col. 5 |
| 15 | " | Same Formula as IX Col. 4 |

Signed and Sealed this

Sixth Day of November, 1990

Attest:

HARRY F. MANBECK, JR.

Attesting Officer    Commissioner of Patents and Trademarks